(12) United States Patent
Hansson et al.

(10) Patent No.: US 9,000,125 B2
(45) Date of Patent: Apr. 7, 2015

(54) APPROACH TO TREAT INTRAOCULAR HYPERTENSION

(76) Inventors: Hans-Arne Hansson, Hovås (SE); Stefan Lange, Göteborg (SE); Eva Jennische, Göteborg (SE)

( * ) Notice: Subject to any disclaimer, the term of this patent is extended or adjusted under 35 U.S.C. 154(b) by 222 days.

(21) Appl. No.: 13/469,838

(22) Filed: May 11, 2012

(65) Prior Publication Data

US 2012/0283191 A1    Nov. 8, 2012

Related U.S. Application Data

(60) Division of application No. 12/289,388, filed on Oct. 27, 2008, now Pat. No. 8,207,296, which is a continuation of application No. PCT/SE2007/000414, filed on Apr. 27, 2007.

(30) Foreign Application Priority Data

Apr. 27, 2006    (SE) ..................................... 0600932

(51) Int. Cl.
  *C07K 7/06*    (2006.01)
  *A61K 38/17*   (2006.01)

(52) U.S. Cl.
  CPC .................. *A61K 38/1709* (2013.01)

(58) Field of Classification Search
  USPC ........................................ 530/329, 324, 328
  See application file for complete search history.

(56) References Cited

U.S. PATENT DOCUMENTS

| | | | |
|---|---|---|---|
| 6,020,143 A | 2/2000 | St. George-Hyslop et al. | |
| 6,344,440 B1 | 2/2002 | Lonnroth et al. | |

FOREIGN PATENT DOCUMENTS

| | | | |
|---|---|---|---|
| WO | WO 95/08992 A1 | 4/1995 | |
| WO | WO 96/17602 A1 | 6/1996 | |
| WO | WO 97/08202 A1 | 3/1997 | |
| WO | WO 98/21978 A1 | 5/1998 | |
| WO | WO 00/38535 A1 | 7/2000 | |
| WO | WO 2005/030246 A1 | 4/2005 | |
| WO | WO 2007/126363 A2 | 11/2007 | |
| WO | WO 2007/126365 A2 | 11/2007 | |

OTHER PUBLICATIONS

Rajendran, Lawrence et al., "Raft Association and Lipid Droplet Targeting of Flotillins are Independent of Caveolin", Biol. Chem., vol. 388, pp. 307-314; Mar. 2007.
Alvarado, J.A. et al., "A New Insight Into the Cellular Regulation of Aqueous Outflow", www.bjophthalmol.com, Dec. 13, 2007, XP-002462343, pp. 1500-1505.
Freeman, Michael R. et al., "Transit of Hormonal and EGF Receptor-Dependent Signals Through Cholesterol-Rich Membranes" www.elsevier.com, Steroids 72 (2007) pp. 210-217.
Marquez, Diana C., et al., Estrogen Receiptors in Membrane Lipid Rafts and Signal Transduction in Breast Cancer Molecular and Cellular Endocrinology 246 (2006) pp. 91-100.
Helms, J. Bernd and Zurzolo, Chiara; Lipids As Targeting Signals: Lipid Rafts and Intracellular Trafficking; Traffic 2004, vol. 5, Blackwell Munksgaard, pp. 247-254.
Chini, B and Parent, M; "G-Protein Coupled Receptors in Lipid Rafts and Caveolae: How, When and Why Do They Go There" Journal of Molecular Endocrinology (2004) 32, pp. 325-338.
Triantafilou, Kathy and Triantafilou, Martha; "Lipid-Raft-Dependent Coxsackievirus B4 Internalization and Rapid Targeting to the Golgi", Virology 326 (2004) pp. 6-19.
Pohl, Jurgen et al; "Long-Chain Fatty Acid Uptake Unto Adipocytes Depends on Lipid Raft Function", Biochemistry 2004, 43, pp. 4179-4187.
Dermine, Jean-Francois et al, "Flotillin-1-Enriched Lipid Raft Domains Accumulate on Maturing Phagosomes", The Journal of Biological Chemistry, vol. 276, No. 21, May 25, 2001, pp. 18507-18512.
Kurzchalia, Teymuras V. and Parton, Robert G., "Membrane Microdomains and Caveolae", Current Opinion in Cell Biology, 1999, pp. 424-431.

*Primary Examiner* — David Lukton
(74) *Attorney, Agent, or Firm* — Cermak Nakajima & McGowan LLP; Malcolm K. McGowan

(57) ABSTRACT

The present invention relates to the use of antisecretory factors, such as antisecretory proteins, homologues, derivatives and/or fragments thereof having antisecretory activity, for the manufacture of a pharmaceutical composition for use in the treatment and/or prevention of intraocular hypertension. The invention thus relates to the use of pharmaceutical compositions comprising antisecretory factors in the treatment and/or prevention of intraocular hypertension, which is preferably characterized by hampered outflow of body fluid resulting in elevated pressure in the eye. The invention provides for a novel approach for treating and/or preventing such a condition turning the intraocular pressure to an acceptable level, optionally 21 mm Hg, or less.

19 Claims, 5 Drawing Sheets

```
Met Val Leu Glu Ser Thr Met Val Cys Val Asp Asn Ser Glu Tyr Met
1               5                   10                  15
Arg Asn Gly Asp Phe Leu Pro Thr Arg Leu Gln Ala Gln Gln Asp Ala
            20                  25                  30
Val Asn Ile Val Cys His Ser Lys Thr Arg Ser Asn Pro Glu Asn Asn
            35                  40                  45
Val Gly Leu Ile Thr Leu Ala Asn Asp Cys Glu Val Leu Thr Thr Leu
            50                  55                  60
Thr Pro Asp Thr Gly Arg Ile Leu Ser Lys Leu His Thr Val Gln Pro
65              70                  75                  80
Lys Gly Lys Ile Thr Phe Cys Thr Gly Ile Arg Val Ala His Leu Ala
            85                  90                  95
Leu Lys His Arg Gln Gly Lys Asn His Lys Met Arg Ile Ile Ala Phe
            100                 105                 110
Val Gly Ser Pro Val Glu Asp Asn Glu Lys Asp Leu Val Lys Leu Ala
            115                 120                 125
Lys Arg Leu Lys Lys Glu Lys Val Asn Val Asp Ile Ile Asn Phe Gly
            130                 135                 140
Glu Glu Glu Val Asn Thr Glu Lys Leu Thr Ala Phe Val Asn Thr Leu
145                 150                 155                 160
Asn Gly Lys Asp Gly Thr Gly Ser His Leu Val Thr Val Pro Pro Gly
            165                 170                 175
Pro Ser Leu Ala Asp Ala Leu Ile Ser Ser Pro Ile Leu Ala Gly Glu
            180                 185                 190
Gly Gly Ala Met Leu Gly Leu Gly Ala Ser Asp Phe Glu Phe Gly Val
            195                 200                 205
Asp Pro Ser Ala Asp Pro Glu Leu Ala Leu Ala Leu Arg Val Ser Met
            210                 215                 220
Glu Glu Gln Arg His Ala Gly Gly Ala Arg Arg Ala Ala Arg Ala
225                 230                 235                 240
Ser Ala Ala Glu Ala Gly Ile Ala Thr Thr Gly Thr Glu Asp Ser Asp
            245                 250                 255
Asp Ala Leu Leu Lys Met Thr Ile Ser Gln Gln Glu Phe Gly Arg Thr
            260                 265                 270
Gly Leu Pro Asp Leu Ser Ser Met Thr Glu Glu Gln Ile Ala Tyr
            275                 280                 285
Ala Met Gln Met Ser Leu Gln Gly Ala Glu Phe Gly Gln Ala Glu Ser
            290                 295                 300
Ala Asp Ile Asp Ala Ser Ser Ala Met Asp Thr Ser Glu Pro Ala Lys
305                 310                 315                 320
Glu Glu Asp Asp Tyr Asp Val Met Gln Asp Pro Glu Phe Leu Gln Ser
            325                 330                 335
Val Leu Glu Asn Leu Pro Gly Val Asp Pro Asn Asn Glu Ala Ile Arg
            340                 345                 350
Asn Ala Met Gly Ser Leu Pro Pro Arg Pro Pro Arg Thr Ala Arg Arg
            355                 360                 365
Thr Arg Arg Arg Lys Thr Arg Ser Glu Thr Gly Gly Lys Gly
370                 375                 380
```

Fig. 4

SEQUENCE LISTING

```
<160> NUMBER OF SEQ ID NOS: 7

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 1

Val Cys His Ser Lys Thr Arg Ser Asn Pro Glu Asn Asn Val Gly Leu
1               5                   10                  15

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 2
```

```
Ile Val Cys His Ser Lys Thr Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 3

Val Cys His Ser Lys Thr Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 4

Cys His Ser Lys Thr Arg
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 5

His Ser Lys Thr Arg
1               5

<210> SEQ ID NO 6
<211> LENGTH: 382
<212> TYPE: PRT
<213> ORGANISM: Homo sapiens

<400> SEQUENCE: 6

Met Val Leu Glu Ser Thr Met Val Cys Val Asp Asn Ser Glu Tyr Met
1               5                   10                  15

Arg Asn Gly Asp Phe Leu Pro Thr Arg Leu Gln Ala Gln Gln Asp Ala
            20                  25                  30

Val Asn Ile Val Cys His Ser Lys Thr Arg Ser Asn Pro Glu Asn Asn
        35                  40                  45

Val Gly Leu Ile Thr Leu Ala Asn Asp Cys Glu Val Leu Thr Thr Leu
    50                  55                  60

Thr Pro Asp Thr Gly Arg Ile Leu Ser Lys Leu His Thr Val Gln Pro
65                  70                  75                  80

Lys Gly Lys Ile Thr Phe Cys Thr Gly Ile Arg Val Ala His Leu Ala
```

```
                    85                  90                  95
Leu Lys His Arg Gln Gly Lys Asn His Lys Met Arg Ile Ile Ala Phe
                100                 105                 110
Val Gly Ser Pro Val Glu Asp Asn Glu Lys Asp Leu Val Lys Leu Ala
            115                 120                 125
Lys Arg Leu Lys Lys Glu Lys Val Asn Val Asp Ile Ile Asn Phe Gly
        130                 135                 140
Glu Glu Glu Val Asn Thr Glu Lys Leu Thr Ala Phe Val Asn Thr Leu
145                 150                 155                 160
Asn Gly Lys Asp Gly Thr Gly Ser His Leu Val Thr Val Pro Pro Gly
                165                 170                 175
Pro Ser Leu Ala Asp Ala Leu Ile Ser Ser Pro Ile Leu Ala Gly Glu
            180                 185                 190
Gly Gly Ala Met Leu Gly Leu Gly Ala Ser Asp Phe Glu Phe Gly Val
        195                 200                 205
Asp Pro Ser Ala Asp Pro Glu Leu Ala Leu Ala Leu Arg Val Ser Met
210                 215                 220
Glu Glu Gln Arg His Ala Gly Gly Ala Arg Arg Ala Ala Arg Ala
225                 230                 235                 240
Ser Ala Ala Glu Ala Gly Ile Ala Thr Thr Gly Thr Glu Asp Ser Asp
                245                 250                 255
Asp Ala Leu Leu Lys Met Thr Ile Ser Gln Gln Glu Phe Gly Arg Thr
            260                 265                 270
Gly Leu Pro Asp Leu Ser Ser Met Thr Glu Glu Glu Gln Ile Ala Tyr
        275                 280                 285
Ala Met Gln Met Ser Leu Gln Gly Ala Glu Phe Gly Gln Ala Glu Ser
    290                 295                 300
Ala Asp Ile Asp Ala Ser Ser Ala Met Asp Thr Ser Glu Pro Ala Lys
305                 310                 315                 320
Glu Glu Asp Asp Tyr Asp Val Met Gln Asp Pro Glu Phe Leu Gln Ser
                325                 330                 335
Val Leu Glu Asn Leu Pro Gly Val Asp Pro Asn Asn Glu Ala Ile Arg
            340                 345                 350
Asn Ala Met Gly Ser Leu Pro Pro Arg Pro Pro Arg Thr Ala Arg Arg
        355                 360                 365
Thr Arg Arg Arg Lys Thr Arg Ser Glu Thr Gly Gly Lys Gly
370                 375                 380

<210> SEQ ID NO 7
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(34)
<223> OTHER INFORMATION: This region may or may not be present
<220> FEATURE:
<221> NAME/KEY: MOD_RES
<222> LOCATION: (35)..(35)
<223> OTHER INFORMATION: May not be present
<220> FEATURE:
<221> NAME/KEY: MOD_RES
<222> LOCATION: (38)..(38)
<223> OTHER INFORMATION: His, Arg or Lys
<220> FEATURE:
<221> NAME/KEY: MOD_RES
<222> LOCATION: (39)..(39)
```

-continued

```
<223> OTHER INFORMATION: Ser or Leu
<220> FEATURE:
<221> NAME/KEY: MOD_RES
<222> LOCATION: (41)..(41)
<223> OTHER INFORMATION: Thr or Ala
<220> FEATURE:
<221> NAME/KEY: MOD_RES
<222> LOCATION: (43)..(163)
<223> OTHER INFORMATION: This region, or portions thereof, may or may
      not be present; see specification as filed for detailed
      description

<400> SEQUENCE: 7

Met Val Leu Glu Ser Thr Met Val Cys Val Asp Asn Ser Glu Tyr Met
1               5                   10                  15

Arg Asn Gly Asp Phe Leu Pro Thr Arg Leu Gln Ala Gln Gln Asp Ala
            20                  25                  30

Val Asn Ile Val Cys Xaa Xaa Lys Xaa Arg Ser Asn Pro Glu Asn Asn
        35                  40                  45

Val Gly Leu Ile Thr Leu Ala Asn Asp Cys Glu Val Leu Thr Thr Leu
    50                  55                  60

Thr Pro Asp Thr Gly Arg Ile Leu Ser Lys Leu His Thr Val Gln Pro
65                  70                  75                  80

Lys Gly Lys Ile Thr Phe Cys Thr Gly Ile Arg Val Ala His Leu Ala
                85                  90                  95

Leu Lys His Arg Gln Gly Lys Asn His Lys Met Arg Ile Ile Ala Phe
            100                 105                 110

Val Gly Ser Pro Val Glu Asp Asn Glu Lys Asp Leu Val Lys Leu Ala
        115                 120                 125

Lys Arg Leu Lys Lys Glu Lys Val Asn Val Asp Ile Ile Asn Phe Gly
    130                 135                 140

Glu Glu Glu Val Asn Thr Glu Lys Leu Thr Ala Phe Val Asn Thr Leu
145                 150                 155                 160

Asn Gly Lys
```

APPROACH TO TREAT INTRAOCULAR HYPERTENSION

CROSS-REFERENCE TO RELATED APPLICATION

This application is a Divisional of U.S. patent application Ser. No. 12/289,388, filed Oct. 27, 2008, now U.S. Pat. No. 8,207,296 which is a Continuation of International Application PCT/SE2007/000414, filed Apr. 27, 2007, which claims the benefit of Swedish Patent Application No. 0600932-8 filed Apr. 27, 2006, the entire specification claims and drawings of these applications are incorporated herein by reference for all purposes.

FIELD OF THE INVENTION

The invention relates to the use of pharmaceutical compositions comprising antisecretory factors in the treatment and/or prevention of intraocular hypertension, which is preferably characterized by hampered outflow of body fluid resulting in elevated pressure in the eye. The invention provides for a novel approach for treating and/or preventing such a condition turning the intraocular pressure to an acceptable level, optionally 21 mm Hg, or less. The invention also relates to a method for treating and/or preventing intraocular hypertension by the administration of pharmaceutical compositions comprising antisecretory factors.

BACKGROUND OF THE INVENTION

Elevated pressure levels in the eye are caused by either elevated production of fluid or hampered outflow of fluid from the eye, or alternatively of combinations thereof. The intraocular pressure (IOP) in a mammalian eye is similar for a wide range of species and in the order of 11-21 mm Hg, such as 10-20 mm Hg, such as 12-18 mm Hg. For humans, a normal range is approximately between 11-21 mm Hg. It is considered elevated if exceeding 20 mm Hg, such as 21 mm Hg, such as 21-24 mm Hg, or 22-30 mm Hg for an extended time period. The level of the IOP is regulated by the formation of a fluid, aqueous humour (AH), originating from the blood and transferred via the ciliary processes into the posterior chamber of the eye. The AH passes the vitreous body and the lens in the posterior chamber and then through the pupil into the anterior chamber. From there most of the AH eventually flows to the irido-corneal angle and egresses the eye through the trabecular meshwork via the Schlemm's canal, the aqueous veins and the scleral and episcleral veins. There is an exchange of fluid and metabolites between the AH and e.g. the lens in the posterior chamber and the cornea in the anterior chamber. A minor portion of the AH enters the uveoscleral route, i.e. the iris, ciliary muscle and sclera and eventually mixes with locally produced tissue fluid before leaving the eye (Jerndal, Hansson & Bill, 1990; Oyster, 1999). The IOP is largely monitored by the outflow, while the formation of the AH in adult humans is considered to be less variable. The main regulators of the IOP are the endothelium of the trabecular meshwork, the juxtacanalicular endothelial meshwork and the inner wall endothelium of the canal of Schlemm (Liltjen-Drecoll 1998; Sacca et al 2005). The latter is of special importance in rectifying and monitoring the flow from the anterior chamber to the vascular system. In the endothelial cells, invaginations, named caveolae, are formed and filled with AH, and then chiefly transferred as giant vacuoles through the endothelial cells to eventually empty their content into the canal of Schlemm. Increased IOP results in the formation of a large number of such giant vacuoles and the opposite is true if the IOP is reduced (Jerndal, Hansson & Bill, 1990; Liltjen-Drecoll 1998). Additionally, these cells may tentatively have the ability to monitor their cell volume, thereby further influencing the paracellular leakage of AH (Starner et al., 2001). FIG. 1a shows a schematic figure of the human eye and FIG. 1b a scanning electron micrograph of the irido-corneal angle of a human adult eye.

The term intraocular hypertension is in medical practice used as a diagnosis for a chronic disease with an IOP exceeding 20 mm Hg, such as 21-24 mm Hg, such as 22-30 mm Hg. Patients with intraocular hypertension may suffer from that condition without developing any signs of sequel such as visual field loss or other signs of retinal and optic nerve abnormalities. Acute rise in the IOP may occur transiently at e.g. coughing, high workload, after a trauma to the eye bulb and a Valsalva's manoeuvre. There is normally a diurnal variation of the IOP, being highest in humans at early daytime. In an adult human, about 2-3 µL of AH is formed per minute, resulting in that the AH in an eye is renewed in about 1½ h. That means that the formation and outflow must be monitored within narrow limits to maintain the IOP within the normal range. The IOP must neither become too high or too low. The main functions of the AH are to provide nutrients, oxygen, ions and fluid to e.g. the lens and the cornea and to drain metabolites and debris. Further, the IOP and the AH interact to keep the optical properties and the shape of the eye. The production of AH may be disclosed by several methods, such as by determining the turnover of AH and its outflow. The intraocular pressure is accurately determined by e.g. tonometry.

The presence of abnormal IOP, may be demonstrable in some glaucoma patients. Nonetheless, not all glaucoma patients do show signs of intraocular hypertension. The term intraocular hypertension must thus not be confused with the medical diagnosis of glaucoma. In contrast to intraocular hypertension, glaucoma is defined as a disease characterised by with time increasing detonation and eventually blindness due to progressive loss of retinal nerve cells and degeneration of the optic nerve. A wide range of conditions are included under the term glaucoma, all having in common that they eventually result in detoriation of vision (Ritch et al., 1996). Thus, the diagnosis glaucoma relates to visual loss and not to the presence of abnormal IOP.

The IOP is mainly regulated by the outflow of the AH from the anterior chamber in the eye to the veins through the iridocorneal angle to the Schlemm's canal. If the egress of the AH from the eye is hampered or even blocked, the IOP will become elevated. The resistance to the outflow, normally resulting in an IOP in the range of 10-20 mm Hg, such as 12-18 mm Hg, is mainly localised to the trabecular meshwork and the endothelial lining of the canal of Schlemm. The endothelial cells in the trabecular meshwork and Schlemm's canal interact in the regulation of the outflow of AH (Alvarado et al., 2005; Jerndal et al., 1991). There is no direct communication between the anterior chamber on one hand and the Schlemm's canal, including the scleral and episcleral veins, on the other. In subjects with intraocular hypertension the trabecular meshwork is characterized by degeneration to a variable extent, accumulation of sheath-derived plaque material and increased resistance to outflow of the AH (Rohen et al, 1993). Further, accumulation of pigments and exfoliation material as well as of blood cells and clot may in certain cases as well add to and further hamper the outflow, elevating the IOP. Hypersecretion, i.e. excessive formation of AH, is a rare sole cause of intraocular hypertension. Thus, improved, sustained control of the turn over of AH, especially the control of the outflow of AH through the iridocorneal angle is of key importance in lowering and normalizing the IOP, in order to monitor intraocular hypertension.

Available therapies for the treatment of intraocular hypertension in clinical practice aim to preferably increase the outflow of AH, but some drugs, such as e.g. dorzolamide and brinzolamide, decrease the AH production. A few of the presently used drugs influence both the formation and the outflow paths. It ought to be stressed that the composition as well as the turn over of AH is of importance as AH supplies e.g. the lens and the cornea with nutrients, fluid and oxygen and takes care of formed vast products. Side effects are prevalent with presently used drugs and often hamper adequate treatment. Additionally, there are subjects with intraocular hypertension, who are not possible to treat adequately by available drugs. Thus, there is a need of therapeutic approaches for lowering the IOP to normal levels.

The antisecretory protein is a 41 kDa protein, originally described to provide protection against diarrhoeal diseases and intestinal inflammation (for a review, see Lange and Lönnroth, 2001). The antisecretory protein has been sequenced and its cDNA cloned. The antisecretory activity seems to be mainly exerted by a peptide located between 1-163, or more specifically, between the positions 35 and 50 on the antisecretory protein amino acid sequence. Immunochemical and immunohistochemical investigations have revealed that the antisecretory protein is present in and may also be synthesized by most tissues and organs in a body. Synthetic peptides, comprising the antidiarrheoic sequence, have been characterized (WO 97/08202; WO 05/030246). Antisecretory factors have previously been disclosed to normalize pathological fluid transport and/or inflammatory reactions, such as in the intestine and the choroid plexus in the central nervous system after challenge with the cholera toxin (WO 97/08202). Addition of antisecretory factors to food and feed was therefore suggested to be useful for the treatment of oedema, diarrhoea, dehydration and inflammation in WO 97/08202. WO 98/21978 discloses the use of products having enzymatic activity for the production of a food that induces the formation of antisecretory proteins. WO 00/038535 further discloses the food products enriched in antisecretory proteins as such.

Antisecretory protein and fragments thereof have also been shown to improve the repair of nervous tissue, and proliferation, apoptosis, differentiation, and/or migration of stem and progenitor cells and cells derived thereof in the treatment of conditions associated with loss and/or gain of cells (WO 05/030246).

The present inventors have now surprisingly found that antisecretory factor protein, homologues and peptide fragments derived thereof reduce the resistance to outflow of the AH through the iridocorneal angle of the eye to the venous system. This presents a new therapeutical application for antisecretory proteins, homologues and fragments thereof, i.e. the use of such proteins and fragments in the preparation of medicaments for the treatment and/or prevention of intraocular hypertension.

SUMMARY OF THE INVENTION

The present invention relates to the use of pharmaceutical compositions comprising antisecretory factors in the treatment and/or prevention of intraocular hypertension. The invention is based on the finding that antisecretory factors, i.e. antisecretory proteins and peptides, derivatives, homologues and fragments thereof having antisecretory activity, increase the outflow of fluid in the eye, thereby reducing the intraocular pressure.

In a first aspect the present invention relates to the use of an antisecretory protein or a homologue, derivative or fragment thereof having antisecretory activity, or a pharmaceutically acceptable salt thereof for the manufacture of a pharmaceutical composition for the prevention and/or treatment of intraocular hypertension.

In a second aspect the present invention relates to a method for treating and/or preventing intraocular hypertension in a mammal, wherein the method comprises administering an effective amount of a pharmaceutical composition comprising an antisecretory protein or a homologue, derivative or fragment thereof having antisecretory activity, or a pharmaceutically acceptable salt thereof to a mammal in need thereof.

BRIEF DESCRIPTION OF THE DRAWINGS

FIG. 4 shows the amino acid sequence of an antisecretory protein according to SEQ ID NO 6 of the present invention. The sequence corresponds to SEQ ID NO 2 from U.S. Pat. No. 6,344,440.

DEFINITIONS

Figure 1A:
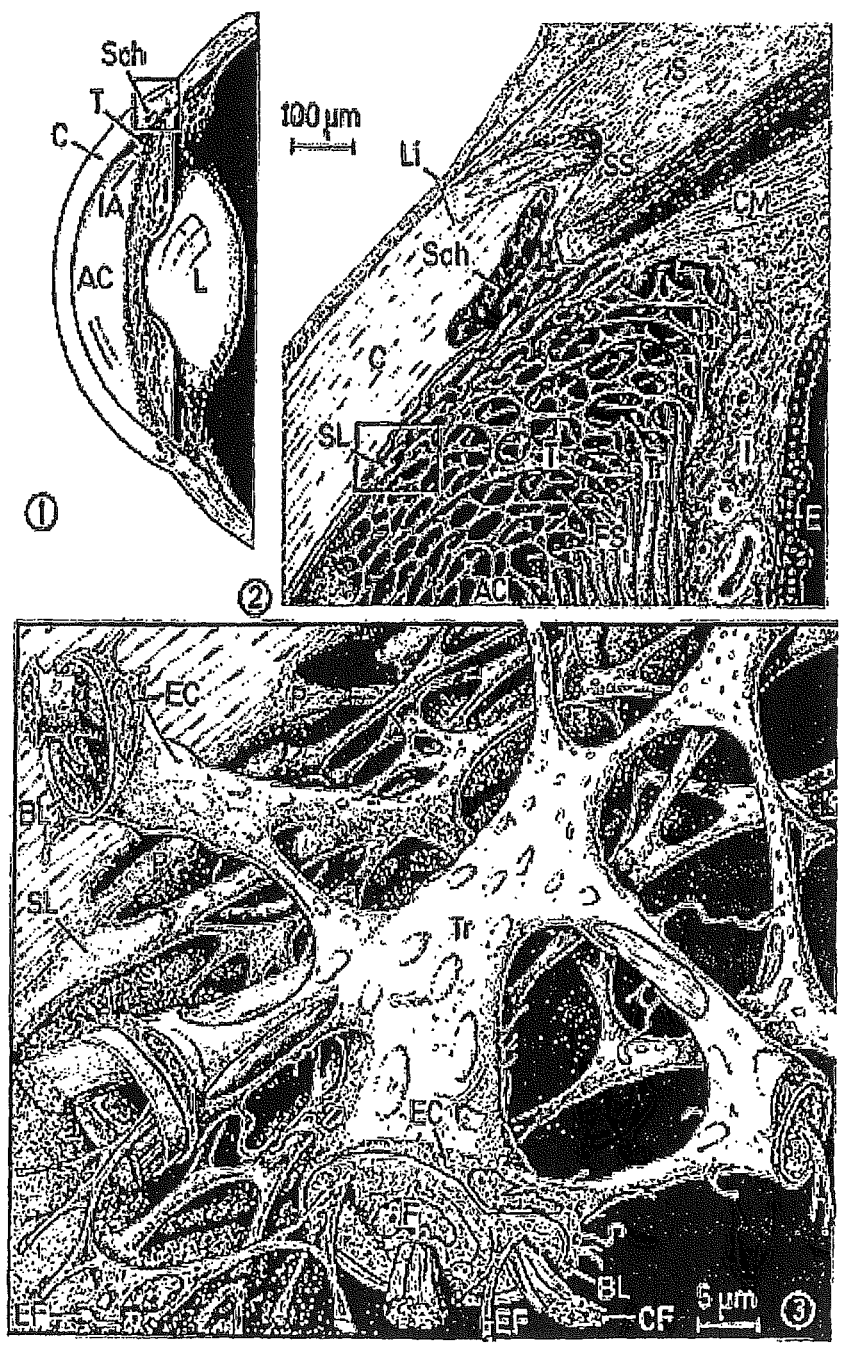
FIG. 1a shows a schematic figure of a human eye (1-1). The Schwann's canal (Sch) is seen at higher magnification, separated from the anterior chamber (AC) by the trabecular meshwork (T) (1-2). Also disclosed is that each trabeculum (Tr) is enveloped by endothelial cells (EC) (1-3). The aqueous humour is formed at the ciliary processes seen to the right of the framed area in FIG. 1-1. L=lens; C=cornea; I=iris; S=sclera; Modified from: R. V. Krstid, 1991.
Figure 1B:
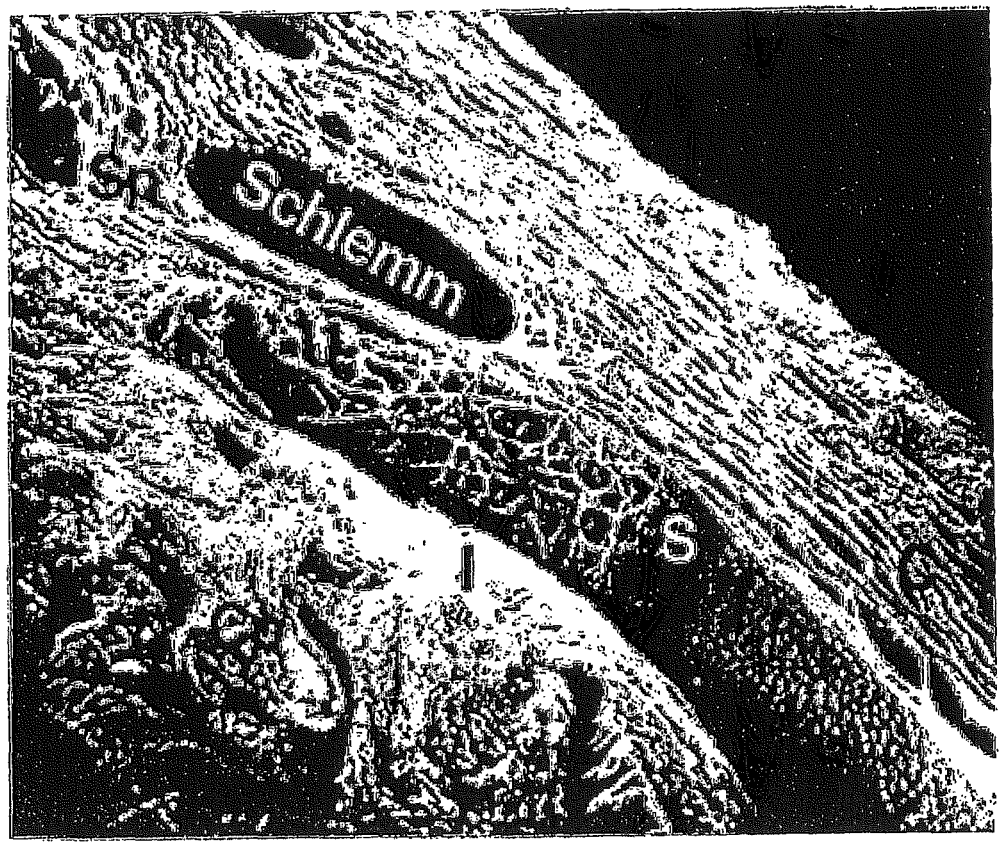
FIG. 1b is a scanning electron micrograph of the iridocorneal angle of a human eye from a 55 year old man, who had his eye enucleated due to a retrobulbar tumour. The trabecular meshwork, marked U, is seen separated from the Schlemm's canal by fairly dense tissue. C=cornea; Sp=scleral spur; I=iris; Cp=ciliary processes; S=line of Schwalbe. The air is at the top right. From Jerndal et al., 1991.

In the present application the anterior [eye] chamber is defined as the space between the anterior surface of the iris and the endothelial surface of the cornea, connected at the iridocorneal angle. The posterior [eye] chamber is defined as the space between the anterior surface of the vitreous body and the lens and the posterior surface of the iris. The posterior chamber and the anterior chamber are connected through the pupil.

Antisecretory protein in the present context refers to a protein with antisecretory properties as previously defined in WO97/08202 and WO 00/38535.

In the present context antisecretory factor(s) (AF) refers to an antisecretory protein or a peptide or a homologue, derivative and/or fragment thereof having antisecretory activity. In the present context, such a peptide, homologue, derivative or fragment has analogous biological activity in the treatment and/or prevention of intraocular hypertension. Antisecretory factors have previously been disclosed e.g. in WO 97/08202 and WO 05/030246. In the present context the terms antisecretory factor, antisecretory factor protein, antisecretory protein, antisecretory peptide, antisecretory derivative and antisecretory fragment are used interchangeably. Also intended by the term antisecretory factor is egg yolk enriched in antisecretory factors as disclosed in SE 900028-2 and WO 00/38535 as further described below.

By aqueous humour, AH, is meant a watery fluid formed from the blood at the ciliary processes, flowing through the posterior chamber and the pupil into the anterior chamber and then leaving the anterior chamber via chiefly the trabecular meshwork and the canal of Schlemm and eventually venous blood vessels.

CNS is the central nervous system, comprising the brain and the spinal cord.

By oedema is meant the accumulation of excessive amount of watery fluid in cells, tissues or serous cavities (see e.g. Stedman's Medical Dictionary, 5$^{th}$ ed., Lippincott, Williams & Wilkins, Philadelphia, 2005).

By glaucoma is meant group of diseases characterized by progressive damage to the retina and to the optic nerve, resulting in loss and narrowing of the visual field and eventually loss of vision. Intraocular pressure (IOP) is the pressure exerted by the aqueous humour in the eye ball. Intraocular hypertension is a condition at which the pressure in the eye ball exceeds 20 mm Hg, such as 21 mm Hg, such as 22-30 mm Hg in an awake subject. Thus, in the present context, the wording intraocular hypertension is used interchangeably with abnormal intraocular pressure. By intraocular hypotension is meant that the pressure in the eyeball is less than 11 mm Hg, such as 10 mm Hg in an awake subject.

Iridocorneal angle is the junction in the anterior chamber between the iris and the posterior part of the cornea.

PBS is phosphate buffered saline.

In the present context the terms "treatment" or "treating" relates to the therapeutic treatment in order to cure or alleviate a condition of intraocular hypertension. Also intended in the present invention is the "prevention" of intraocular hypertension, which pertains to the prophylactic treatment for avoiding the occurrence of intraocular hypertension.

By trabecular meshwork is meant the meshwork of trabeculae and sheets of collagenous connective tissue lined by endothelial cells, interposed at the iridocorneal angle between the anterior chamber and the Schlemm's canal.

By Schlemm's canal is meant the circular venous channel in the outer portion of the internal scleral sulcus at the limbus region of the eye, connected via the aqueous humour veins to the venous draining system of the eye. Sclemm's canal is the main outflow system for the aqueous humour from the anterior chamber of the eye.

Proteins are biological macromolecules constituted by amino acid residues linked together by peptide bonds. Proteins, as linear polymers of amino acids, are also called polypeptides. Typically, proteins have 50-800 amino acid residues and hence have molecular weights in the range of from about 6,000 to about several hundred thousand Dalton or more. Small proteins are called peptides or oligopeptides. The term "protein" and "peptide" may be used interchangeably in the present context.

A "pharmaceutical composition", in the present context, refers to a composition comprising a therapeutically active amount of an antisecretory protein, optionally in combination with a pharmaceutically active excipient, such as a carrier or a vehicle. Said pharmaceutical composition is formulated for the appropriate route of administration, which may vary depending on the condition of the patient, as well as on other factors, such as age or preferred choice. A pharmaceutical composition comprising an antisecretory protein serves as a drug delivery system. The pharmaceutical composition upon administration presents the active substance to the body of a human or an animal. Pharmaceutical compositions suitable for the present invention are further described below.

DETAILED DESCRIPTION OF THE INVENTION

The present invention is based on the surprising finding that antisecretory factors (AF), such as antisecretory protein and homologues, derivatives or fragments thereof cause a reduction of the resistance to outflow of the aqueous humour through the iridocorneal angle of the eye to the venous system, which increases the outflow of abnormally accumulated fluid in the eye. Thereby the outflow of aqueous humour is increased, leading to a decrease in the intraocular pressure in the eye. This presents a new therapeutical application for antisecretory proteins and fragments thereof, i.e. the use of such proteins and fragments in the preparation of pharmaceutical compositions for the treatment and/or prevention of intraocular hypertension. The use of the pharmaceutical compositions according to the present invention is likely to be most useful to patients at risk for developing or suffering from intraocular hypertension.

As described above, the outflow of aqueous humour mainly occurs through the angle of the iris and is regulated by the cells that form the trabecular meshwork. Most of the aqueous humour is transported out of the eye via the Schlemm's canal. The aqueous humour is transported enclosed in small vesicles through the cells of the trabecular meshwork to the Schlemm's canal, as well as to some extent paracellularly. Additionally and to a minor extent the AH leaves the eye through the angle structures of the iris and the sclera. The flow out of the eye of aqueous humour, in which "small portions" of liquid is transported at a time, is radically different from the transport of ions and water in e.g. the intestine, wherein ion and water pumps of the epithelial cells of the intestine transport one molecule at the time. Therefore, although antisecretory factors have previously been suggested for use in the treatment of conditions such as oedema, diarrhea, dehydration, glaucoma and inflammation (WO 97/08202), the mechanism of action of antisecretory factors in the treatment of these diseases is different from their mechanism of action according to the present invention, wherein the resistance to outflow of aqueous humour through the iridocorneal angle of the eye to the venous system is reduced by the antisecretory factors. However, it should be noted though, that intraocular hypertension in a later stage may or may not result in glaucoma.

In a first aspect, the present invention therefore relates to the use of an anti secretory protein and/or a homologue, derivative or fragment thereof having antisecretory activity, i.e. an antisecretory factor, and/or a pharmaceutically acceptable salt thereof for the manufacture of a pharmaceutical composition for the prevention and/or treatment of intraocular hypertension. The antisecretory factor is a protein that occurs naturally in the body. The human antisecretory factor is a 41 kDa protein, comprising 382 amino acids when isolated from the pituitary gland. The active site with regard to the intraocular pressure decreasing effect according to the present invention seems to be localized in a region close to the N-terminal of the protein, localized to amino acids 1-163 of SEQ ID NO 6, or to fragments of this region.

The present inventors have shown that the antisecretory factor is to some extent homologous with the protein S5a, also named Rpn 10, which constitute a subunit of a constituent prevailing in all vertebrate cells, the 26 S proteasome, more specifically in the 19 S/PA 700 cap. In the present invention, antisecretory proteins are defined as a class of homologus proteins having the same functional properties. The proteasomes have a multitude of functions related to the degradation of surplus proteins as well as short-lived, unwanted, denatured, misfolded and otherwise abnormal proteins. Further, the antisecretory factor/S5a/Rpn10 is involved in the cellular distribution and transportation of cell constituents, most evidently proteins, as further described in commonly available textbooks.

Homologues, derivatives and fragments of antisecretory proteins and/or peptides according to the present invention all have analogous biological activity of being able to decrease the intraocular pressure. Antisecretory homologues, derivatives and fragments, in the present context, comprise at least 4 amino acids of a naturally occurring antisecretory protein, which may be further modified by changing one or more amino acids in order to optimize the antisecretory factor's biological activity in the treatment and/or prevention of intraocular hypertension.

A fragment of an antisecretory protein will generally comprise the peptide/amino acid sequence or a fragment thereof in a preparation in which more than 90%, e.g. 95%, 96%, 97%, 98% or 99% of the protein in the preparation is a protein, peptide and/or fragments thereof of the invention.

Furthermore, any amino acid sequence being at least 70% identical, such as being at least 72%, 75%, 77%, 80%, 82%, 85%, 87%, 90%, 91%, 92%, 93%, 94%, 95%, 96%, 97%, 98%, or 99% identical with the amino acid sequence of a antisecretory protein, peptide, homologue, derivative and/or fragment according to the invention, is also considered to be inside the scope of the present invention. In the present context the terms homologous and identity are used interchangeably, i.e. an amino acid sequence having a specified degree of identity with another amino acid sequence has the same degree of homology to a specified amino acid sequence.

In the present context a derivative is intended to be a protein having antisecretory activity as defined herein, being derived from another substance either directly or by modification or partial substitution, wherein one or more amino acids have been substituted by another amino acid, which amino acid can be a modified or an unnatural amino acid. Such modified and/or unnatural amino acids are well known to the person skilled in the art. For example, the antisecretory factor derivatives according to the invention may comprise an N terminal and/or a C terminal protecting group. One example of an N terminal protecting group includes acetyl. One example of a C terminal protecting group includes amide.

By a proteins, homologues, derivatives, peptides and/or fragment thereof having an amino acid sequence at least, for example 95% identical to a reference amino acid sequence, it is intended that the amino acid sequence of e.g. the peptide is identical to the reference sequence, except that the amino acid sequence may include up to 5 point mutations per each 100 amino acids of the reference amino acid sequence. In other words, to obtain a polypeptide having an amino acid sequence at least 95% identical to a reference amino acid sequence, up to 5% of the amino acids in the reference sequence may be deleted or substituted with another amino acid, or a number of amino acids up to 5% of the total amino acids in the reference sequence may be inserted into the reference sequence.

These mutations of the reference sequence may occur at the amino or carboxy terminal positions of the reference amino acid sequence or anywhere between those terminal positions, interspersed either individually among amino acids in the reference sequence or in one or more contiguous groups within the reference sequence.

In the present invention, a local algorithm program is best suited to determine identity. Local algorithm programs, (such as Smith-Waterman) compare a subsequence in one sequence with a subsequence in a second sequence, and find the combination of subsequences and the alignment of those subsequences, which yields the highest overall similarity score. Internal gaps, if allowed, are penalized. Local algorithms work well for comparing two multidomain proteins, which have a single domain or just a binding site in common.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F. et al, Altschul, S. F. et al (1990)). Each sequence analysis program has a default scoring matrix and default gap penalties. In general, a molecular biologist would be expected to use the default settings established by the software program selected.

The antisecretory proteins or a peptide or a homologue, derivative or fragment thereof having antisecretory activity according to the present invention can be of 4 amino acids or more, such as 5-16 amino acids, 6, 7, 8, 9, 10, 11, 12, 13, 14, 15, 16, 17, 18, 19 or 20 amino acids or more. In other preferred embodiments the antisecretory factor consists of 42, 43, 45, 46, 51, 80, 128, 129 or 163 amino acids. In preferred embodiments the antisecretory factor consists of 5, 6, 7, 8 or 16 amino acids.

In another preferred embodiment, the antisecretory protein, peptide and/or homologue, derivative or fragment thereof having antisecretory activity according to the present invention consists of a sequence according to the following formulae (SEQ ID NO: 7):

X1-V-C-X2-X3-K-X4-R-X5 wherein X1 is I, amino acids 1-35 of SEQ ID NO 6, or is absent, X2 is H, R or K, X3 is S or L, X4 is T or A, X5 is amino acids 43-46, 43-51, 43-80 or 43-163 of SEQ ID NO 6, or is absent. The antiseqretory factor according to the present invention can be produced in vivo or in vitro, e.g. recombinantly, chemically synthesized, and/or isolated from a naturally occurring source of antisecretory factors, such as from pig pituitary glands or birds' eggs. After production, the antisecretory factors may be further processed, such as by chemical or enzymatic cleavage to smaller antisecretory active fragments or by modification of amino acids. It is presently not possible to obtain antisecretory factor in pure form by purification. It is however possible to produce a biologically active antisecretory factor protein recombinantly as previously disclosed in WO 97/08202 and WO 05/030246. WO 05/030246 and WO 97/08202 also disclose the production of biologically active fragments of this protein.

The antisecretory factor according to the invention may further comprise an N terminal and/or a C terminal protecting group. One example of an N terminal protecting group includes acetyl. One example of a C terminal protecting group includes amide.

The term "pharmaceutically active salt", refers to a salt of an antisecretory protein, which may be any salt derived there from, based on so called Hofmeiser series. Since proteins and peptides are amphoteric, without limiting the scope of invention, the term "pharmaceutically acceptable salt" thus when stored, e.g. as trifluoroacetate or acetate, also refers to a more stable form of an antisecretory factor according to the invention.

The pharmaceutical composition or medicament of the invention may additionally comprise one or more pharmacologically acceptable carriers, excipient or diluents, such as those known in the art.

The compositions or medicaments may be in form of, for example, fluid, semi-fluid, semisolid or solid compositions such as, but not limited to, dissolved transfusion liquids, such as sterile saline, various salt solution, glucose solutions, phosphate buffer saline, blood, plasma or water, powders, microcapsules, micro spheres, nanoparticles, sprays, aerosols, inhalation devices, solutions, dispersions, suspensions, emulsions and mixtures thereof. The compositions may take into consideration the stability and reactivity of the peptides or of the protein.

The pharmaceutical compositions of the invention may be formulated according to conventional pharmaceutical practice, e.g. according to "Remington: The science and practice of pharmacy", 21$^{st}$ edition, ISBN 0-7817-4673-6 or "Encyclopedia of pharmaceutical technology", 2" edition, ed. Swarbrick J., ISBN: 0-8247-2152-7.

In one preferred embodiment of the present invention the antisecretory factor is an antisecretory protein with an amino acid sequence as shown in SEQ ID NO 6 or a homologue, derivative and/or fragment thereof comprising amino acids 38-42 of SEQ ID NO 6.

In a preferred embodiment of the present invention the antisecretory factor is a selected among SEQ ID NO 1-6, i.e. VCHSKTRSNPENNVGL (SEQ ID NO 1, in this context also called AF-16), IVCHSKTR (SEQ ID NO 2); VCHSKTR (SEQ ID NO 3), CHSKTR (SEQ ID NO 4), HSKTR (SEQ ID NO 5), or the amino acid sequence of an antisecretory protein according to SEQ ID NO 6 (also shown in FIG. 4) using the common one letter abbreviations for amino acids. SEQ ID NO 1, 2, and 3 have previously been disclosed in e.g. WO 05/030246 and SEQ ID NO 6 in U.S. Pat. No. 6,344,440. As specified in the accompanying sequence listing, some of the amino acids in the above specified sequences may be replaced by other amino acids. In the following the position of a particular amino acid in a particular amino acid sequence is calculated from the left, denoting the most N-terminal amino acid as being in position 1 in that particular sequence. Any amino acid substitution(s) as specified below may be performed independently of any other amino acid substitution(s) in that sequence. In SEQ ID NO 1, the C in position 2 may be replaced by S, H in position 3 may be replaced with R or K, S in position 4 may be replaced with L, and/or T in position 6 may be replaced with A. In SEQ ID NO 2, C in position 3 may be replaced by S, H in position 4 may be replaced by R or K, S in position 5 may be replaced by L, and/or T in position 7 may be replaced by A. In SEQ ID NO 3, C in position 2 may be replaced by S, H in position 3 may be replaced by R or K, S in position 4 may be replaced by L, and/or T in position 6 may be replaced by A. In SEQ ID NO 4, C in position 1 may be replaced by S, H in position 2 may be replaced by R or K, S in position 3 may be replaced by L, and/or T in position 5 may be replaced by A. In SEQ ID NO 5, H in position 1 may be replaced by R or K, S in position 2 may be replaced by L, and/or T in position 4 may be replaced by A.

In one preferred embodiment of the present invention said fragment comprises an amino acid sequence as shown in SEQ ID NO 1.

In one preferred embodiment of the present invention said fragment comprises an amino acid sequence as shown in SEQ ID NO 2.

In one preferred embodiment of the present invention said fragment comprises an amino acid sequence as shown in SEQ ID NO 3.

In one preferred embodiment of the present invention said fragment comprises an amino acid sequence as shown in SEQ ID NO 4.

In one preferred embodiment of the present invention said fragment comprises an amino acid sequence as shown in SEQ ID NO 5.

Also intended by the present invention is the combination of two or more of any of the antisecretory factors according to the present invention, optionally also in combination with egg yolk enriched in antisecretory factors.

In one preferred embodiment of the present invention the antisecretory factor is used for the manufacture of a pharmaceutical composition for the treatment and/or prevention of, or in a method of treating and/or preventing intraocular hypertension, wherein the intraocular tension is 21 mm Hg or more, such as 22 mm HG or more. In another preferred embodiment of the present invention, the intraocular tension is normal or even low, i.e. below 21-24 mm Hg, preferably below 10-12 mm Hg, such as between 11-21 mmHg. An IOP less than 11 mm Hg, such as less than 10 mm Hg, such as less than 10-12 mm Hg, is considered as lower than the normal, i.e. being low. The beneficial effects of the administration of pharmaceutical compositions according to the present invention also to mammals having an intraocular pressure which is normal, or even below normal, is that also such mammals may have peaks in the intraocular pressure over the day, which can then be treated and/or prevented by the pharmaceutical compositions of the invention. In another preferred embodiment the intraocular tension is exceeding 21 mm Hg, such as 21-24 mm Hg, such as 22-30 mm Hg.

Also intended by the present invention is the possibility of treating and/or preventing intraocular hypertension and/or preparing a pharmaceutical composition using egg yolk enriched in antisecretory factors. SE 9000028-2 discloses how the formation of antisecretory factors can be stimulated in birds and antisecretory factors then being recovered or concentrated from digests of egg yolk. WO 00/38535 further discloses how such recovered or concentrated antisecretory factors can be administered to animals or humans with a food or feed, or, as more or less isolated products, formulated into pharmaceutical products. Therefore, also intended in the present application is the use of egg yolk enriched in antisecretory factors for the preparation of products, such as pharmaceutical compositions, for treating and/or preventing intraocular hypertension or for use in such a method of treatment. In a preferred embodiment said antisecretory protein is provided in a concentration of at least 1000 FIL units/ml in said egg yolk. In the present context one FIL unit corresponds to a 50% reduction of the fluid flow in the intestine compared to a control without supply of antisecretory factors, as disclosed in WO 00/38535 and SE 9000028-2. The antisecretory factor(s) according to the present invention can therefore also be administered in the form of a "medical food". In the present context, medical food refers to a food, which has been prepared with a composition with an antisecretory protein. Said food may be any suitable food, in fluid or solid form, such as a liquid or a powder, or any other suitable food stuff. Examples of such matter may be found in WO 00/38535.

In one preferred embodiment of the present invention the intraocular hypertension to be treated and/or prevented is caused by a resistance in the outflow of aqueous humour from the anterior chamber of the eye.

In another preferred embodiment the pharmaceutical composition used according to the present invention reduces the resistance in outflow of aqueous humour from the anterior chamber through the trabecular meshwork and the Schlemm's canal.

In one embodiment of the present invention the pharmaceutical composition according to the invention further comprises a pharmaceutically acceptable excipient. The choice of pharmaceutically acceptable excipients and their optimum concentration for use according to the present invention can readily be determined by the skilled person by experimentation. Pharmaceutically acceptable excipients for use according to the present invention include solvents, buffering agents, preservatives, chelating agents, antioxidants, stabilizers, emulsifying agents, suspending agents and/or diluents.

A pharmaceutically acceptable excipient is a substance, which is substantially harmless to the individual to which the composition will be administered. Such an excipient normally fulfils the requirements given by the national drug agencies. Official pharmacopoeias such as the United States of America Pharmacopoeia and the European Pharmacopoeia set standards for well-known pharmaceutically acceptable excipients.

The following is a review of relevant pharmaceutical compositions for use according to the invention. The review is based on the particular route of administration. However, it is appreciated that in those cases where a pharmaceutically acceptable excipient may be employed in different dosage forms or compositions, the application of a particular pharmaceutically acceptable excipient is not limited to a particular dosage form or of a particular function of the excipient.

Parenteral Compositions:

For systemic application, the compositions according to the invention may contain conventional non-toxic pharmaceutically acceptable carriers and excipients, including microspheres and liposomes.

The compositions for use according to the invention may include all kinds of solid, semisolid and fluid compositions.

The pharmaceutically acceptable excipients may include solvents, buffering agents, preservatives, chelating agents, antioxidants, stabilizers, emulsifying agents, suspending agents and/or diluents. Examples of the different agents are given bellow, Example of Various Agents Examples of solvents include but are not limited to water, alcohols, blood, plasma, spinal fluid, ascites fluid and lymph fluid.

Examples of buffering agents include but are not limited to citric acid, acetic acid, tartaric acid, lactic acid, hydrogenphosphoric acid, bicarbontates, phosphates, diethylamine, etc.

Examples of chelating agents include but are not limited to sodium EDTA and citric acid.

Examples of antioxidants include but are not limited to butylated hydroxyl anisole (BHA), ascorbic acid and derivatives thereof, tocopherol and derivatives thereof, cysteine, and mixtures thereof.

Examples of diluents and disintegrating agents include but are not limited to lactose, saccharose, emdex, calcium phosphates, calcium carbonate, calcium sulphate, mannitol, starches and microcrystalline cellulose.

Examples of binding agents include but are not limited to saccharose, sorbitol, gum acacia, sodium alginate, gelatine, starches, cellulose, sodium carboxymethylcellulose, methylcellulose, hydroxypropylcellulose, polyvinylpyrrolidone and polyetyleneglycol.

The pharmaceutical composition or the substance used according to the invention is preferably administered via intravenous peripheral infusion or via intramuscular or subcutaneous injection into the patient or via buccal, pulmonary, nasal, cutaneous or oral routes. Furthermore, it is also possible to administer the pharmaceutical composition or the pharmaceutically active substance through a surgically inserted shunt into a cerebral ventricle of the patient.

In one embodiment the pharmaceutical composition according to the present invention is formulated for intraocular, intranasal, oral, subcutaneous and/or systemic administration. The pharmaceutical compositions can be administered one or more times per day. In a preferred embodiment of the present invention the pharmaceutical composition is formulated for administration as a spray, aerosol, by a nebulizer or by an inhaler. In another preferred embodiment, the composition of the invention is to be administered by application as a suspension or, even more preferably, a powder for inhalation with a spray, aerosol or nebulizer nasally and/or to the respiratory tract. A nebulizer is a medical device that delivers liquid medication in the form of a mist to the airways. Nebulizer compressors force air through tubing into a medicine cup filled with liquid medicine. The force of the air breaks the liquid into tiny mist-like particles that can be inhaled deeply into the airways. The term "aerosol" in the present context, refers to a gaseous suspension of fine solid or liquid particles. The pharmaceutical composition in the form of a powder comprising antisecretory factors has the additional advantages in terms of stability and dosage and that dry powder may be administrated with an inhaler. The pharmaceutical composition can also be topically applied to the eye, intraocularly, intranasally, orally, subcutaneously and/or systemically via blood vessels. In a preferred embodiment, the pharmaceutical composition is formulated for topical administration to the eye. Typically, when used for topical application to the eye, the applied concentration per day in the composition of the invention is from 1 μg to 10 mg per application, such as from 1 μg to 1 mg per application, preferably 50-1000 μg per day, such as 50-500 μg per day, 50-250 μg per day, 100-250 μg per day, 500-250 μg per day, 500-750 μg per day, or 50-100 μg per day, either as a single dose per day or repeated several times per day and eye. When systemically administered to the blood, the dose is typically in the range of 0.1 μg to 10 mg per application and kg body weight and day, such as 0.1 μg to 1 mg per application and kg body weight and day, preferably 1-1000 μg/kg body weight, preferably again 1-100 μg/kg body weight, either as a single dose per day or repeated several times per day. When egg yolk enriched in antisecretory factors is used according to the present invention, this is preferably administered orally. An important feature of the AF protein, peptide, fragment and/or derivative thereof is that no local or systemic side effects have been recognized even at high doses, enabling intense treatment without known risks.

The present invention also relates to the use of an antisecretory protein or a homologue, derivative and/or fragment thereof having antisecretory activity, and/or a pharmaceutically acceptable salt thereof for the manufacture of a pharmaceutical composition for intraocular administration.

The present invention also relates to a peptide as shown in SEQ ID NO 4, a homologue, derivative and/or fragment thereof per se. The invention further relates to the use of a peptide according to SEQ ID NO 4 for medical use.

The present invention also relates to a peptide as shown in SEQ ID NO 5, a homologue, derivative and/or fragment thereof per se. The invention further relates to the use of a peptide according to SEQ ID NO 5 for medical use. Such a peptide is also disclosed in a copending application from the same applicant for use for the preparation of a pharmaceutical composition for use in the treatment and/or prevention of compartment syndrome.

The present invention also relates to a method for treating and/or preventing intraocular hypertension in a mammal in need thereof, said method comprising administering an effective amount of a pharmaceutical composition comprising an antisecretory protein, a homologue, derivative and/or fragment thereof having antisecretory activity, and/or a pharmaceutically acceptable salt thereof. Pharmaceutical compositions for use in such a method are as disclosed above.

The present invention therefore relates to a method for treating and/or preventing intraocular hypertension in a mammal in need thereof, said method comprising administering an effective amount of a pharmaceutical composition comprising an antisecretory protein, a homologue, derivative and/or fragment thereof having antisecretory activity, and/or a pharmaceutically acceptable salt thereof.

In a preferred embodiment the method according to the present invention comprises administering said pharmaceutical composition intraoculary.

In a preferred embodiment of the method according to the present invention said pharmaceutical composition comprises one or more of the fragments comprising an amino acid sequence as shown in SEQ ID NO 1-6.

In a preferred embodiment of the method according to the present invention said antisecretory protein consists of a sequence according to the following formulae (SEQ ID NO: 7):

X1-V-C-X2-X3-K-X4-R-X5 wherein X1 is I, amino acids 1-35 of SEQ ID NO 6, or is absent, X2 is H, R or K, X3 is S or L, X4 is T or A, X5 is amino acids 43-46, 43-51, 43-80 or 43-163 of SEQ ID NO 6, or is absent.

In a preferred embodiment of the method according to the present invention the antisecretory protein is a protein with an amino acid sequence as shown in SEQ ID NO 6, a homologue, derivative and/or fragment thereof comprising amino acids 38-42 of SEQ ID NO 6.

In a preferred embodiment of the method according to the present invention, said fragment of an anti secretory protein comprises an amino acid sequence as shown in SEQ ID NO 1.

In a preferred embodiment of the method according to the present invention, said fragment of an antisecretory protein comprises an amino acid sequence as in SEQ ID NO 2.

In a preferred embodiment of the method according to the present invention said fragment of an antisecretory protein comprises an amino acid sequence as in SEQ ID NO 3.

In a preferred embodiment of the method according to the present invention said fragment of an antisecretory protein comprises an amino acid sequence as in SEQ ID NO 4.

In a preferred embodiment of the method according to the present invention said fragment of an antisecretory protein comprises an amino acid sequence as in SEQ ID NO 5.

In a preferred embodiment of the method according to the present invention, said pharmaceutical composition comprises two or more of any of the antisecretory factors according to the present invention, optionally also in combination with egg yolk enriched in antisecretory factors.

In a preferred embodiment of the method according to the present invention the intraocular tension in the mammal is 21 mm Hg or more.

In a preferred embodiment of the method according to the present invention the intraocular tension is normal or low.

In a preferred embodiment of the method according to the present invention the antisecretory protein is provided in egg yolk enriched in such antisecretory protein, and said antisecretory protein is preferably provided in a concentration of at least 1000 FIL units/ml in said egg yolk.

In a preferred embodiment of the method according to the present invention the intraocular hypertension is caused by a resistance in the outflow of aqueous humour from the anterior chamber of the eye.

In a preferred embodiment of the method according to the present invention the pharmaceutical composition reduces the resistance in outflow of aqueous humour from the anterior chamber through the trabecular meshwork and the Schlemm's canal.

In a preferred embodiment of the method according to the present invention the pharmaceutical composition further comprises a pharmaceutically acceptable excipient.

In a preferred embodiment of the method according to the present invention the pharmaceutical composition is formulated for intraocular, intranasal, oral, subcutaneous and/or systemic administration.

In a preferred embodiment of the method according to the present invention the pharmaceutical composition is formulated as a spray, aerosol, or for administration by a nebulizer or an inhaler.

In a preferred embodiment of the method according to the present invention the pharmaceutical composition is administered systemically to the blood at a dose of 0.1 μg to 10 mg per application and kg body weight and day, preferably 1-1000 μg per application and kg body weight. An important feature of the AF protein, peptide, fragment and/or derivative thereof is that no local or systemic side effects have been recognized even at high doses, enabling intense treatment without known risks.

In an equally preferred embodiment of the method according to the present invention the pharmaceutical composition is administered systemically to the blood at a dose of 0.1 μg to 10 mg per application and kg body weight and day, such as at a dose of 0.1 μg to 1 mg per application and kg body weight and day, preferably 1-100 μg per application and kg body weight.

In a preferred embodiment of the method according to the present invention the pharmaceutical composition is formulated for topical administration to the eye.

In a preferred embodiment of the method according to the present invention, the pharmaceutical composition is administered locally at a dose of 1 μg to 10 mg per application, preferably 50-1000 μg, per day.

In an equally preferred embodiment of the method according to the present invention the pharmaceutical composition is administered at a dose of 0.1 μg to 10 mg per application and kg body weight and day, such as at a dose of 1 μg to 1 mg per application, preferably 50-250 μg, per day.

In a preferred embodiment of the method according to the present invention the pharmaceutical composition is administered one or more times per day.

EXPERIMENTAL SECTION

Example 1

Young adult rabbits (New Zealand White, NZW) had their diurnal rhythm adjusted by exposing the animals to darkness from 9 AM to 9 PM, while the light was on from 9 PM to 9 AM. Thereby, the dynamics of the IOP was known, as the IOP in normal rabbits is increasing at the onset of darkness. Unilateral deposition of 10-50 μg AF-16 (SEQ IN NO 1) (dissolved in PBS with 10 or 50% ethanol added) between the eye bulb and the Tenon's capsule resulted in anaesthetized rabbits in a transient drop of the IOP by 2.5 mm Hg in 2 h, as determined with the aid of a TonoPen® (Medtronic Inc., Minneapolis Minn., USA). The dye fluorescein (Sigma-Aldrich, Inc, St. Louis, Mo., USA; sodium salt, dissolved in PBS) was injected intravenously and the appearance of the tracer determined with an operation microscope, equipped with a slit lamp arrangement. There was no difference with regard to the time of appearance of the dye fluorescein between the eye treated with AF-16 and the opposite eye, treated with just the vehicle. The described procedure was repeated and the same result documented. Similar IOP reducing effect was achieved with a higher dose, 100 µg AF-16. Thus, it is concluded that the production of the AH was obviously not markedly affected by the AF-16 treatment, as reflected by the fact that the used tracer, fluorescein, could be demonstrated to appear about concomitantly in the AF-16 treated and the vehicle treated eyes, respectively.

Example 2

Young adult NZW rabbits had their diurnal rhythm adjusted by exposing the animal to darkness from 9 AM to 9 PM, while the light was on from 9 PM to 9 AM. Thereby, the dynamics of the IOP was known. Unilateral deposition by injection of 10-50 µg AF-16 (dissolved in 50 or 100 µL PBS with 10 or 50% ethanol added) between the eye bulb and the Tenon's capsule temporally in two anaesthetized rabbits resulted in 2 hours in a drop of the IOP by 2.5 mm Hg, as determined with the aid of a TonoPen®. Then, 20 or 50 µL of a solution in PBS, containing 3% Evans blue (Merck, Sigma) and 2% bovine serum albumin (Sigma), was injected into both eyes through the pars plana into border between the posterior eye chamber and the vitreous body. Ophthalmic sutures were enclosing the injection sites to prevent reflux and leakage. The blue dye was observed to enter the anterior chamber and to leave the eye through the episcleral veins, more rapidly in the eye pre-treated with AF-16 than in the opposite eye just treated with the vehicle. The experiment was repeated once the next day with the same result. Thus, the outflow of the AH, as visualized by the albumin-dye-complex through the iridocorneal angle into the canal of Schlemm and its connecting veins, was seemingly facilitated by the application of the peptide AF-16.

Example 3

Anaesthetized adult animals will have the flow of AH and the resistance to outflow determined according to the perilimbal suction cup technique, an established and repeatedly published approach. Additional approaches will be used to determine these parameters. Quantitative and qualitative figures will thereby be obtained regarding the effects of AF-16 on the dynamics of the AH and the IOP in normal animals and animals with experimentally elevated IOP. The same is true for animals with congenital intraocular hypertension.

Example 4

Young adult NZW rabbits had their diurnal rhythm adjusted by exposing the animals to darkness from 9 AM to 9 PM, while the light was on from 9 PM to 9 AM. Thereby, the IOP is elevated by several mm Hg during the first few hours of darkness. Unilateral injection (50-250 µL) of up to 100 µg AF-16, dissolved in PBS, with 10% ethanol added, beneath the Tenon's capsule to the anaesthetized animals caused in one hour a significant drop in the IOP, by up to 5 mm Hg, as compared to the IOP in the opposite eye, which just had the vehicle (PBS with 10% ethanol) deposited. The reduction in the IOP after treatment with AF-16 persisted for at least 4 h, and then turned equal to that of the opposite eye as determined the next day. These results were possible to repeat for 3 consecutive days, and on 3 rabbits. It is concluded that AF-16 efficiently reduce the IOP in a normal eye with a few mm Hg, corresponding to what has been reported to be achieved with other drugs aimed to lower the IOP.

Example 5

Young adult NZW rabbits had their diurnal rhythm adjusted by exposing the animals to darkness from 9 AM to 9 PM, while the light was on from 9 PM to 9 AM. Thereby, the diurnal dynamics of the IOP was known. Unilateral deposition twice with 2 min interval of 25 µg AF-16 (in all 50 µg), in 25 µL phosphate buffered saline (PBS), in the formix conjunctivae inferior (cul-de-sac) to anaesthetized animals resulted after one hour in a drop of the IOP by 1.5-2.5 mm Hg, as compared to the IOP in the opposite eye, which just had the vehicle, PBS, deposited. The reduction in the IOP after treatment with AF-16 persisted for at least 4 h, and then turned equal to that of the opposite eye the next day. These results were possible to repeat during 2 consecutive days, and on 2 rabbits. Thus, these experiments demonstrate that local deposition of AF-16 in the cul-de-sac of normal rabbits result in a transient lowering of the IOP.

Example 6

Young adult NZW rabbits had their diurnal rhythm adjusted by exposing the animals to darkness from 9 AM to 9 PM, while the light was on from 9 PM to 9 AM. Thereby, the diurnal dynamics of the IOP was known. Unilateral deposition twice with 2 min interval of 50 µg AF-16 (in all 100 µg), in 50 µL PBS, in the lower cul-de-sac (formix conjunctivae inferior) to the anaesthetized animals resulted after one hour in a drop in the IOP by 2-4 mm Hg, as compared to the IOP in the opposite eye, which had had the vehicle deposited. The reduction in the IOP after treatment with AF-16 persisted for at least 4 h, and then turned equal to that of the opposite eye the next day. These results were possible to repeat during 3 consecutive days, and on 2 rabbits. It is concluded that local treatment of a normal eye with a dose double that of AF-16, as stated in Example 5, as well transiently reduced the IOP, with no recognized obvious local or systemic side effects.

Example 7

The objective of this experiment, performed on behalf of the applicant by Visionar AB, Uppsala, Sweden, was to study the dynamics of the IOP in rabbits after topical treatment with AF-16, and to compare achieved effects with that of the drug Timolol® (2.5 mg/mL; Alcon Sweden AB, Stockholm, Sweden), known to reduce intraocular hypertension, and the vehicle, PBS. Twenty albino female NZW rabbits, weighing 2.1-2.4 kg, were purchased and housed individually in single cages with free access to food (K1, Lactamin, Stockholm, Sweden) and tap water. The daylight cycle was regulated by having the light on between 9 AM and 9 PM. During the 3 weeks long acclimatization period, the animals were trained daily in the test situation of measuring the IOP after having had local anaesthesia applied to their corneae.

The animals were randomized into two groups:

Group 1, (n=10). These animals got 2 drops of AF-16 (in all 50 µg, in 50 µL PBS) in one eye and equal volume, 2×25 µL, of the vehicle, PBS, in the opposite eye. Group 2, (n=10).

These animals got 1 drop (50 µL of Timolol®; 125 µg) in one eye and equal volume PBS in the other eye. Timolol® is known to reduce intraocular pressure in rabbits and therefore was used to validate the model, as a reference. The IOP was measured by a TonoPen XL® (Medtronic) after applying 1 drop of Tetrakain Chauvin® (Novartis Ophthalmics, Taby, Sweden) on each cornea as a local anesthetic. In the final protocol, thus two series of measurements were scheduled. One series after 5 days of local treatment with AF-16 and the vehicle, and another series after 5 days of local treatment with Timolol® or the vehicle.

Figure 2:
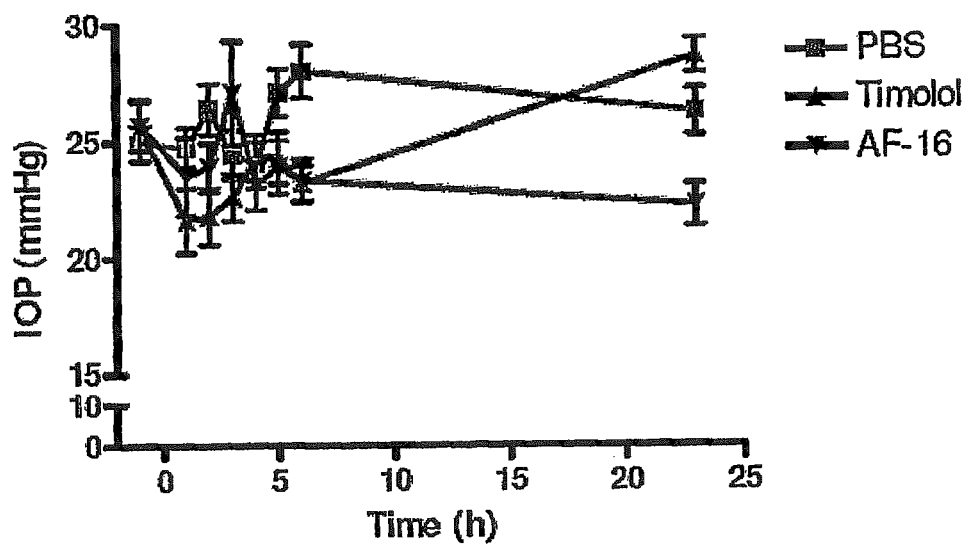
FIG. 2 shows the intraocular pressure at topical treatment of eyes of rabbits with AF-16 (upside-down triangles), the drug Timolol® (triangles), and PBS vehicle (squares), respectively, according to Example 7.

At the first measurement an IOP lowering effect of Timolol® was expected to be found at the 5th and the 6th measurement since the IOP was expected to rise due to the diurnal cycle. The last day of IOP measurements were performed during an extended period (1, 2, 3.25, 4.25, 5.5, 6.5, 7.75, 9, and 10 h after the beginning of the darkness in the animal room) to make sure that data could be obtained during an extended period. The results are presented in the attached FIG. 3. The IOP at the start of the 5 day treatment period is shown in FIG. 2. No adverse effects or complications were recognized at treatment with AF-16, either locally or systemically.

Figure 3:
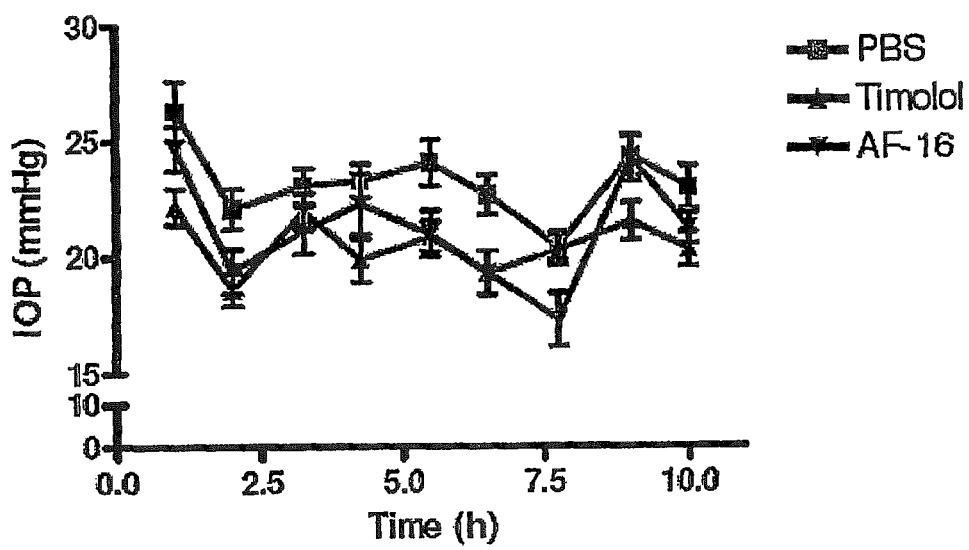
FIG. 3 shows the intraocular pressure after 5 days of topical treatment of eyes of rabbits with AF-16 (upside-down triangles), the drug Timolol® (triangles), and PBS vehicle (squares), respectively, according to Example 7.

It is evident from the data that AF-16 had a lowering effect on the IOP, significantly differing from the IOP measured after treatment with just the vehicle, PBS. The highly significant effects exerted by AF-16 were comparable to those of Timolol® (FIG. 3). It is concluded that these data indicate that AF-16 may be as effective to lower the IOP in rabbits as the commonly used drug (Timolol®), known to have such effects. Thus AF-16 may be useful in the treatment of intraocular hypertension in humans.

Example 8

Two young normal adult NZW rabbits (2.4-2.9 kg, female) had their diurnal rhythm adjusted by exposing the animals to darkness from 9 AM to 9 PM, while the light was on from 9 PM to 9 AM. Thereby, the diurnal dynamics of the TOP was known. Unilateral deposition twice with 2 min interval of 50 or 100 µg of the synthetic hexa-peptide CHSKTR (SEQ ID NO: 4) (in all 100-200 µg), each time in 50 µL PBS, in the lower cul-de-sac (fornix conjunctivae inferior) to the anaesthetized animals resulted after one hour in a drop in the IOP by 2-3 mm Hg, as compared to the IOP in the opposite eye, which just had the vehicle deposited. The reduction in the IOP after treatment with the hexapeptide persisted for at least 2 h, and then turned equal to that of the opposite eye as determined the next day. These results were possible to achieve on 2 rabbits. It is concluded that local treatment of a normal eye with a synthetic peptide, deposited in the lower lacrimal sac, and having parts of the active sequence of antisecretory protein of SEQ ID NO 6, CHSKTR (SEQ ID NO 4), reduces the IOP.

Example 9

Two normal, young adult NZW rabbits (2.4-2.9 kg, female) had their diurnal rhythm adjusted by exposing the animals to darkness from 9 AM to 9 PM, while the light was on from 9 PM to 9 AM. Thereby, the diurnal dynamics of the IOP was known. The anaesthetized animals had unilaterally 50 or 100 µg of the synthetic hexa-peptide CHSKTR (SEQ ID NO: 4), dissolved in 100 µl PBS with 10% ethanol, injected in a temporal position below the Tenon's capsule, which resulted after 30 minutes in a drop in the IOP by 2-4 mm Hg, as compared to the IOP in the opposite eye, which concomitantly had had the vehicle similarly deposited. The reduction in with the hexa-peptide persisted for at least 2 h. The IOP was in both animals equal to that of the opposite eye as determined the next day. These results were possible to achieve on two subsequent days. It is concluded that local treatment of a normal eye by injecting the test substance on the outside of the eyeball, with a synthetic peptide, having parts of the active sequence of the antisecretory protein of SEQ ID NO 6, CHSKTR (SEQ ID NO 4), reduced the IOP, without inducing any local or systemic side effects.

Example 10

Young adult NZW rabbits had their diurnal rhythm adjusted by exposing the animals to darkness from 9 AM to 9 PM, while the light was on from 9 PM to 9 AM. Thereby, the diurnal dynamics of the IOP was known. Intravenous injection of AF-16, at either of two dose levels, 50 or 100 or 1000 µg/kg body weight, dissolved in PBS with 10% ethanol added, to anaesthetized rabbits resulted after one hour in a drop in the IOP by 2-3 mm Hg in either eye, as compared to the IOP measured just before the injection of the AF-16. The reduction in the IOP after treatment with AF-16 persisted for at least 2 h. There was no obvious difference in the IOP between the left and right eye of these animal. The IOP was measured in either eye once more the next day and had returned to close to the values from the day before prior to the AF-16 treatment. No apparent side effects were noticed. It is concluded that intravenous injection of AF-16 at either 50, 100 or, most efficiently, 1000 µg/kg body weight resulted in a reduction of the IOP, demonstrable in an hour and persisting for several h and that the IOP returned to the original level in a day. Both eyes of the treated rabbits showed the same dynamic pattern with regard to the effects of AF on the IOP. It is concluded that the peptide AF-16 if administrated intravenously, i.e. systemically, efficiently lower the IOP, but to an acceptable extent, so far without causing an abnormally low IOP.

Example 11

Young adult NZW rabbits had their diurnal rhythm adjusted by exposing the animals to darkness from 9 AM to 9 PM, while the light was on from 9 PM to 9 AM. Thereby, the diurnal dynamics of the IOP was known. Intranasal deposition of AF-16, 50, 100 or 1000 µg/kg body weight, dissolved in PBS, was performed on 3 anaesthetized rabbits and resulted in an hour in a drop in the IOP by at least 2 mm Hg in either eye, as compared to the IOP measured just before the deposition of AF-16 in a nostril. The reduction in the IOP after treatment with high dose of AF-16 persisted for 2 and 3 h, the time periods investigated. There was no difference in the IOP between the left and right eye of the same animal. The IOP was measured in either eye once more the next day and demonstrated to have returned to about the values from the day before prior to the AF-16 treatment. No apparent side effects were noticed. It is concluded that intranasal infusion of up to 1000 µg/kg of AF-16 will result in a reduction of the IOP, demonstrable within 1 h and persisting for at least 3 h and that the IOP returned to the original level in a day. Both eyes in each rabbit show the same pressure patterns. No local or systemic side effects were noticed.

Example 12

Young adult NZW rabbits had their diurnal rhythm adjusted by exposing the animals to darkness from 9 AM to 9

PM, while the light was on from 9 PM to 9 AM. Thereby, the diurnal dynamics of the IOP was monitored to be known. While under general anaesthesia such a rabbit had 10 g of freeze dried egg yolk enriched in the AF-protein (Salovum™ dissolve in diluted, commercial orange juice) deposited in the stomach. Such an intragastric deposition of AF proteins resulted in an hour in a drop of the IOP in either eye, as compared to the IOP measured just before the deposition of Salovum™. There was no difference in the IOP between the left and right eye of the animal. The IOP was measured in either eye once more the next day and had returned to about the values from the day before prior to the AF-16 treatment. No apparent side effects are likely to be noticed. It is concluded that oral ingestion of egg yolk which is enriched in antisecretory proteins, e.g. Salovum™, resulted in a reduction of the IOP, demonstrable within roughly one hour and persisting for a few h and that the IOP returned to the original level in a day. Both eyes showed the same IOP pattern.

Example 13

A young adult NZW rabbit with unilateral slight buphthalmos (enlarged left eye ball) was anaesthetized and had its IOP measured with the aid of a TonoPen® tonometer. The IOP in the buphthalmic eye was 30-32 mm Hg while that in the normal opposite eye was 11-12 mm Hg, as repeatedly investigated. Unilateral injection of 50 µg AF-16 in 100 µL PBS with 10% ethanol temporally beneath the Tenon's capsule to the anaesthetized animals resulted in an hour in a reduction of the IOP to 14-16 mm Hg. Injection of the same amount of AF-16 to the opposite eye resulted in a drop of just about 2 mm Hg, as determined with a TonoPen®. The IOP in the left buphthalmic eye had the next day increased to just above 30 mm Hg, i.e. returned to its original level. Injection once more of AF-16 resulted in 2 hours again in an IOP of 15-16 mm Hg, while the same dose of AF-16 reduced the IOP in the right eye just 1-2 mm Hg. No adverse reactions could be recognized. It is thus concluded that local deposition by injection at the eye ball transiently lowers the elevated intraocular pressure to normal levels in a buphthalmic eye.

Example 14

Young adult NZW rabbits had their diurnal rhythm adjusted by exposing the animal to darkness from 9 AM to 9 PM, while the light was on from 9 PM to 9 AM. Thereby, the dynamics of the IOP was synchronized with the diurnal alterations in the IOP. Exposure of such rabbits to a sagittal rotational acceleration impulse, as described in a recent publication in a scientific medical international journal (Krave U, Höjer S & Hansson H.-A., European J Neuroscience, 21, 2867-2882, 2005) have been disclosed during the present investigation to injure the eye in addition to causing a diffuse brain injury. Exposure of an anaesthetized rabbits head to an anterior to posterior sagittal rotational acceleration impulse or a posterior to anterior sagittal rotational acceleration impuls at a force of up to 200 krad/s$^2$ resulted in a mechanical distortion and force load on the eye. The IOP increased during the next 30 minutes to 35-40 mm Hg, as determined with a TonoPen® tonometer on anaesthetized animals and stayed elevated for a few hours. Deposition of 100 µg per kg body weight of AF-16 by injecting a solution of AF-16 (100 µL PBS with 10% ethanol) between the Tenon's capsule and the sclera of the temporal region of the eye 10-30 minutes after the sagittal rotational acceleration impact resulted within an hour in the return of the IOP to roughly normal levels. The IOP in the opposite eye, which did not receive any AF-16, remained elevated.

The exposure of rabbits to such a sagittal rotational acceleration impulse results in extensive cytoskeletal alterations in e.g. nerve cells and vascular cells (Hamberger et al., 2003). The same has previously been demonstrated after exposure of pig brains to high energy loads (Suneson et al., 1990). It is therefore concluded that membrane changes as well as cytoskeletal alterations in cells in the trabecular meshwork and Schlemm's canal, induced by the rotational acceleration trauma, resulted in transiently impaired outflow of AH from the anterior chamber, generating transiently elevated IOP. Local treatment with the peptide AF-16 seemed to ameliorates the raised IOP.

Example 15

Rats will have 3 of their 4 episcleral veins unilaterally obliterated. Thereby, the venous blood from the anterior segment of the operated eye will have only one single vein for the efflux of blood from the anterior eye segment. That treatment will in a few weeks result in elevated IOP in the treated eye. The eyes with elevated IOP will be treated topically and/or systemically with AF-16 in PBS in order to determine whether such treatment with AF-16 will normalize the IOP. Such results will enable calculation of the rate of AH formation and outflow characteristics, thereby making it possible to localise the site of action of the AF-16 in the path of the AH flow through the eye.

Example 16

Additional rats will have hypertonic saline injected in the temporal episcleral vein while the other 3 episcleral veins have their blood flow transiently blocked. That treatment will in a few weeks result in elevated IOP in the treated eyes, according to what has been described in the literature by Morrison et al. Eyes with elevated IOP will be treated topically and/or systemically with AF-16 in PBS in order to determine whether such treatment with AF-16 will normalize the IOP. Such results will enable calculation of the rate of AH formation and outflow characteristics, thereby making it possible to localise the site of action of the AF-16 in the path of the AH flow through the eye.

Example 17

Certain strains of rodents, some of which transgenic, have been bred to develop increased intraocular pressure in a high frequency. The effects of AF-16, applied topically, locally and or systemically, on the IOP will be evaluated. Such results will enable calculation of the rate of AH formation and outflow characteristics, thereby making it possible to localise the site of action of the AF-16 in the path of the AH flow through the eye. The use of such animals is considered to constitute a standard approach to evaluate drugs aimed for treatment of intraocular hypertension.

SUMMARY AND CONCLUSIONS

The experiments described unequally disclose that treatment with the antisecretory factors reduce and even normalize elevated pressures in a mammalian eye. This shows the utility of drugs comprising antisecretory factors, proteins, peptides, homologues and fragments, in clinical practice to control elevated IOP in patients with intraocular hypertension. The antisecretory factor AF-16 was experimentally disclosed to efficiently normalize the pressure in eyes with elevated IOP. The main effect of AF-16 is considered to be exerted by its ability to improve the outflow of aqueous humour. It is thus concluded that AF-16 has been revealed to lower and normalize intraocular hypertension by facilitating the egress of AH through the cells in trabecular meshwork and the canal of Schlemm.

REFERENCES

1. Alvarado J A, Alvarado R G, Yeh R F, Franse-Carman L, Marcellino G R, & Brownstein M J. A new insight into the cellular regulation of aqueous outflow: how trabecular meshwork endothelial cells drive a mechanism that regulates the permeability of Schlemm's canal endothelial cells. Brit. J Ophthalmol 89, 1500-1505, 2005.
2. Hamberger A, Huang Y-L, Zhu H, Bao F, Ding M, Blennow K, Olsson A, Hansson H.-A., Viano D & Haglid K G. Redistribution of neurofilaments and accumulation of 13-amyloid protein after brain injury by rotational acceleration of a head. J Neurotrauma 20, 169-178, 2003.
3. Hogan M J, Alvarado J A & Weddell J E. Histology of the human eye. W B Saunders Co., Philadelphia, Pa., USA, 1971
4. Jerndal T, Hansson H-A & Bill A. Goniodysgenesis; a new perspective on glaucoma. Scriptor, Copenhagen, Denmark, 1990
5. Krave U, Höjer S & Hansson H.-A. Transient powerful pressures are generated in the brain by a rotational acceleration impulse to the head. Europ. J Neuroscience, 21, 2876-2882, 2005.
6. Krstic R V. Human microscopic anatomy. Springer Verlag, Berlin, 1991.
7. Lang G K: Ophthalmology. Thieme, Stuttgart, Germany, 2000.
8. Lange S, & Lönnroth I. The antisecretory factor: synthesis, anatomical and cellular distribution, and biological action in experimental and clinical studies. Intern Rev. Cytology 210, 39-75, 2001.
9. Lötjen-Drecoll E. Functional morphology of the trabecular meshwork in primate eyes. Progress Retinal Eye Research 18, 91-119, 1998.
10. Morrison J C, Johnson E C, Cepurna W, & Jia L. Understanding mechanisms of pressure-induced optic nerve damage. Progress Retinal Eye Research 24, 217-240, 2005.
11. Oyster C W. The human eye; structure and function. Sinauer Associates Inc, Sunderland, Mass., USA, 1999.
12. Ritch R, Shields M B & Krupin T. The glaucomas, $2^{nd}$ edition, Mosby, St. Louis, Miss. USA, 1996.
13. Rohen J W, Lötjen-Drecoll E, Flugel C, Meyer M & Grierson I. Ultrastructure of the trabecular meshwork in untreated cases of primary open-angle glaucoma (POAG). Exp Eye Res., 56, 683-692, 1993.
14. Sacca S C, Pascotto A, Camicione P, Capris P, & Izzotti A. Oxidative DNA damage in the human trabecular meshwork. Arch Ophthalmology 123, 458-463, 2005.
15. Salmon J F & Kanski J J. Glaucoma, $3^{rd}$ ed., Butterworth & Heinemann, Edinburgh, 2004.
16. Stamer W D, Peppel K, O'Donnell M E, Roberts B C, Wu F, & Epstein D L. Expression of aquaporin-1 in human trabecular meshwork cells: role in resting cell volume. Invest Ophthalmol. 42, 1803-1811, 2001.
17. Suneson A, Hansson H-A & Seeman T. Pressure wave injuries to the nervous system caused by high energy missile extremity impact. Part II. Distant effects on the central nervous system—a light and electron microscopic study on pigs. J Trauma 30, 295-306, 1990.
18. WO 05/030246
19. WO 97/08202
20. WO 98/21978
21. U.S. Pat. No. 6,344,440

The invention claimed is:

1. A method of treating intraocular hypertension comprising administering to a subject in need of such treatment in an amount sufficient to decrease intraocular pressure a composition comprising an antisecretory factor (AF) protein of SEQ ID NO:6, or a fragment or homologue thereof comprising SEQ ID NO:4, and a pharmaceutically acceptable excipient.

2. The method of claim 1, wherein said protein comprises SEQ ID NO: 6.

3. The method of claim 1, wherein said protein comprises SEQ ID NO: 1.

4. The method of claim 1, wherein said protein comprises SEQ ID NO: 2.

5. The method of claim 1, wherein said protein comprises SEQ ID NO: 3.

6. The method of claim 1, wherein said protein comprises SEQ ID NO: 4.

7. The method of claim 1, wherein said composition comprises two or more of the proteins as in any of claims 1-6.

8. The method of claim 1, wherein the intraocular pressure is 22 mm Hg or more.

9. The method of claim 1, wherein the intraocular pressure is 22-30 mm Hg.

10. The method of claim 1, wherein said protein is provided in egg yolk enriched in said protein, and wherein said antisecretory protein preferably is provided in a concentration of at least 1000 FIL units/ml in said egg yolk, wherein one FIL unit corresponds to a 50% reduction of the fluid flow in the intestine as compared to a control without supply of antisecretory factors.

11. The method of claim 1, wherein said composition is formulated for topical, intraocular, intranasal, oral, subcutaneous, cutaneous, mucosal and/or systemic administration.

12. The method of claim 1, wherein said composition is formulated for administration as a spray, aerosol, by a nebulizer, or by an inhaler.

13. The method of claim 1, wherein said composition is administered systemically to the blood at a dose per application of 0.1 µg to 10 mg per kg of body weight per day, preferably 1-1000 µg per application per kg of body weight.

14. The method of claim 1, wherein said composition is formulated for topical administration to the eye.

15. The method of claim 1, wherein said composition is administered at a dose of 1 µg to 10 mg per application, preferably 50-1000 µg, per day.

16. The method of claim 1, wherein said composition is administered one or more times per day.

17. The method of claim 1, wherein said protein comprises amino acids 38-42 of SEQ ID NO: 6.

18. The method of claim 1, wherein said fragment or homologue is selected from the group consisting of SEQ ID NO: 1, SEQ ID NO: 2, SEQ ID NO: 3, SEQ ID NO: 4, SEQ ID NO: 5, SEQ ID NO: 6, and SEQ ID NO: 7.

19. The method of claim 1, wherein the amount of said AF protein, or fragment or homologue thereof, is sufficient to reduce resistance in outflow of aqueous humour from the anterior chamber of the subject's eye through the trabecular meshwork and Schlemm's canal.

* * * * *